US00PP19977P2

(12) United States Plant Patent
Skotak et al.

(10) Patent No.: US PP19,977 P2
(45) Date of Patent: May 12, 2009

(54) *NEOREGELIA* PLANT NAMED 'ARDIE'

(50) Latin Name: ***Neoregelia* sp.**
Varietal Denomination: Ardie

(76) Inventors: Chester Skotak, Apdt. 652-4050, Alajuela (CR); Reginald Deroose, Droogte 139, B9940, Evergem (BE)

( * ) Notice: Subject to any disclaimer, the term of this patent is extended or adjusted under 35 U.S.C. 154(b) by 0 days.

(21) Appl. No.: 11/897,748

(22) Filed: Sep. 1, 2007

(51) Int. Cl.
*A01H 5/00* (2006.01)

(52) U.S. Cl. ..... Plt./370
(58) Field of Classification Search ..... Plt./370
See application file for complete search history.

(56) References Cited

U.S. PATENT DOCUMENTS

PP7,713 P * 11/1991 Kuipers ..... Plt./370

OTHER PUBLICATIONS

Rainforest Flora Inc., Neoregelias [retrieved on Jul. 15, 2008]. Retrieved from the Internet: <http://www.rainforest-flora.com/Neoregelias.htm> 5 pp.*

* cited by examiner

*Primary Examiner*—Annette H Para
*Assistant Examiner*—June Hwu

(57) ABSTRACT

A new cultivar of *Neoregelia* plant named 'Ardie' that is characterized by variegated yellow-green leaves with green stripes and green margins and a red secondary basal spot.

1 Drawing Sheet

Botanical Classification: *Neoregelia sp.*
Variety denomination: 'Ardie'.

BACKGROUND OF THE INVENTION

The present invention relates to a new and distinct cultivar of *Neoregelia* plant botanically known as *Neoregelia* and hereinafter referred to by the cultivar name 'Ardie'.

The new cultivar was discovered as a naturally occurring branch mutation of *Neoregelia* 'Martin' (U.S. Plant Pat. No. 10,717). The cultivar 'Ardie' was discovered in 2001 in a cultivated area of Apopka, Fla.

Asexual reproduction of the new cultivar 'Ardie' first occurred by terminal cuttings in a greenhouse in 2002 in Apopka, Fla. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Neoregelia* cultivar 'Ardie'. These traits in combination distinguish 'Ardie' as a new and distinct cultivar apart from other existing known varieties of *Neoregelia.*

1. *Neoregelia* 'Ardie' exhibits variegated yellow-green leaves with green stripes and green margins.
2. *Neoregelia* 'Ardie' exhibits young leaves with a red base and a secondary basal spot above the red base.

The closest comparison cultivar is the parent plant *Neoregelia* 'Martin'. 'Ardie' is distinguishable from 'Martin' by the following characteristics:

1. 'Ardie' exhibits lighter colored yellow-green leaves.
2. 'Ardie' exhibits wider yellow-green stripes than those of 'Martin'.

'Ardie' can be compared to *Neoregelia* 'Devroe' (U.S. Plant Pat. No. 7,713). 'Ardie' is distinguishable from 'Devroe' by the following characteristics:

1. 'Ardie' exhibits longer leaves that have more yellow coloration.
2. 'Ardie' exhibits a larger overall size.

'Ardie' can be compared to *Neoregelia* 'Tricolor'. 'Ardie' is distinguishable from 'Tricolor' by the following characteristics:

1. 'Ardie' exhibits longer leaves that have more yellow coloration.
2. 'Ardie' exhibits a larger overall size.

BRIEF DESCRIPTION OF THE DRAWING

The accompanying photograph illustrates the distinguishing traits of *Neoregelia* 'Ardie'. The plant in the photograph shows an overall view of a 12 month old plant. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Neoregelia* cultivar named 'Ardie'. Data was collected in Apopka, Fla. from 12 month old glass greenhouse grown plants in 13 cm. diameter containers. The time of year was Spring and the average temperature was 72 degrees Fahrenheit during the day and 62 degrees Fahrenheit at night. The light level was natural outdoor light. Color determinations are in accordance with The Royal Horticultural Society Colour Chart 2001 edition, except where general color terms of ordinary dictionary significance are used. The growing requirements are similar to the species. 'Ardie' has not been tested under all possible conditions and phenotypic differences may be observed with variations in environmental, climatic, and cultural conditions, however, without any variance in genotype.

Botanical classification: *Neoregelia* 'Ardie'.
Use: Ornamental Annual.
Parentage: 'Ardie' is a naturally occurring branch mutation of Neoregelia 'Martin'.
Vigor: Moderate.
Growth habit: Broad spreading from a basal rosette.
Plant shape: Flattened.
Suitable container size: 13 cm. pots.
Height: 25.4 cm. in height.
Width: 63.1 cm. in width.
Low temperature tolerance: USDA Zone 10.
High temperature tolerance: 40° Centigrade.
Propagation: Terminal cuttings.
Time to initiate roots in summer: 30 days to initiate roots at 28° Centigrade.
Time to initiate roots in winter: 60 days to initiate roots at 28° Centigrade.
Growth rate: Moderate.
Root system: Fine and fibrous.
Stem:
*Branching habit.*—Basal rosette.
*Pinching.*—Not required.
*Number of branches.*—Average one basal rosette.
Foliage:
*Texture.*—Smooth, moderately glossy.
*Leaf arrangement.*—Rosulate, placed in a basal rosette.
*Compound or single.*—Single.
*Quantity of leaves.*—30 leaves per rosette.
*Leaf shape.*—Linear, arching downward.
*Leaf apex.*—Abruptly acute.
*Leaf base.*—Sheathing.
*Leaf length.*—34.9 cm. in length.
*Leaf width.*—4.3 cm. in width.
*Pubescence.*—Absent.
*Leaf margin.*—Entire, but with some small teeth, 1 tooth per cm; teeth moderately sharp to the touch.
*Young leaf color* (*lower surface*).—151D to 4B, margins and longitudal stripes 143A, base 53A to 53B with a secondary basal spot 53A to 53C 3 mm. above the red base.
*Young leaf color* (*upper surface*).—150B to 4A, margins and longitudal stripes 143A, base 53A to 53B with a secondary basal spot 53A to 53C 3 mm. above the red base.
*Mature leaf color* (*lower surface*).—154C to 154D to 4C, margins and longitudal stripes 137A to 143A.
*Mature leaf color* (*upper surface*).—154C to 154D to 4C, margins and longitudal stripes 137A to 143A.
*Vein color* (*under surface*).—154C to 154D to 4C, margins and longitudal stripes 137A to 143A.
*Vein color* (*upper surface*).—154C to 154D to 4C, margins and longitudal stripes 137A to 143A.
*Venation pattern.*—Parallel.
*Durability of foliage to stress.*—High.
Flower:
*Inflorescence arrangement.*—Short terminal raceme.
*Inflorescence type.*—Raceme.
*Inflorescence height.*—4.9 cm.
*Inflorescence width.*—1.9 cm.
*Flowering habit.*—Continuously.
*Quantity of flowers and buds per plant.*—16.
*Natural flowering season.*—Spring.
*Flower type.*—Single.
*Quantity of flowers per lateral stem.*—1 opened flower.
*Quantity of flower buds per lateral stem.*—15.
*Quantity of flowers and buds per plant.*—66.
*Rate of flower opening.*—5% of the flowers are open at one time.
*Fragrance.*—None.
*Flower bud length.*—3.5 cm. in length.
*Flower bud diameter.*—4 mm. in diameter.
*Flower bud shape.*—Linear.
*Bud color.*—N155A, apex 175A.
*Rate of bud opening.*—3 days.
*Flower aspect.*—Straight upward.
*Flower shape.*—Funnelform.
*Flower dimensions.*—5 mm. in diameter and 3.6 cm. in height.
*Flower longevity.*—Approximately 3 days.
*Petal appearance.*—Smooth, moderately glossy.
*Petal texture.*—Smooth.
*Petal arrangement.*—Rotate.
*Number of petals.*—3.
*Fused or unfused.*—Fused, only upper part is free.
*Petal shape.*—Spathulate.
*Petal margin.*—Entire.
*Petal apex.*—Acute.
*Petal length.*—2.1 cm. in length.
*Petal width.*—3 mm.
*Petal color when opening* (*upper side*).—86A to 86B, base N155A.
*Petal color when opening* (*under side*).—N88C, base N155A.
*Petal color fully opened* (*upper side*).—68B, base N155A.
*Petal color fully opened* (*under side*).—68B, base N155A.
*Petal color fading to.*—77A.
*Self-cleaning or persistent.*—Persistent.
Sepals:
*Number of sepals.*—Average 3.
*Sepal Aspect.*—Rotate.
*Sepal shape.*—Narrow lanceolate, strong involute.
*Sepal margin.*—Entire.
*Sepal apex.*—Long acute.
*Sepal base.*—Cuneate.
*Sepal surface.*—Smooth, glossy.
*Sepal dimensions.*—2.2 cm. in length and 3 mm. in width.
*Young sepal color* (*upper side*).—182C to 182D.
*Young sepal color* (*under side*).—174B to 174C, apex 175A to 175B.
*Mature sepal color* (*upper side*).—182C to 182D.
*Mature sepal color* (*under side*).—174B to 174C, apex 175A to 175B.
Calyx:
*Calyx shape.*—Tubular.
*Calyx dimensions.*—2.2 cm. in length and 5 mm. in diameter.
Peduncle:
*Peduncle dimensions.*—1.3 cm. in length and 9 mm. in diameter.
*Peduncle angle.*—0°.
*Peduncle color.*—N155A.
*Peduncle strength.*—Strong.
Bracts: Under each flower, there is one concave bract.
*Bract dimensions.*—4.6 cm. in length, 1.6 cm. in width and 5 mm. in height.

*Bract tip.*—Acute.
*Bract margin.*—Entire.
*Bract base.*—Sheating.
*Bract color.*—Inner side 181B to 181C, outer side 46A, tip 53A.

Reproduction organs:
*Pedicel length.*—5 mm.
*Pedicel diameter.*—2 mm.
*Pedicel angle.*—2°.
*Pedicel strength.*—Strong.
*Pedicel color.*—N155A.
*Stamen number.*—Average 6.
*Anther shape.*—Linear.
*Anther size.*—Average 5 mm.
*Anther color.*—155D.
*Amount of pollen.*—Very low.
*Pollen color.*—N155A.
*Pistil number.*—Average 1.
*Pistil length.*—Average 1.7 cm. in length.
*Stigma shape.*—Narrow club-shaped.
*Stigma color.*—N155A.
*Style length.*—1.4 cm.
*Style color.*—155C.
*Ovary color.*—N155A.

Disease and pest resistance: Plants of the new cultivar have not been observed for disease and pest resistance.

It is claimed:

1. A new and distinct variety of *Neoregelia* plant named 'Ardie' as described and illustrated.

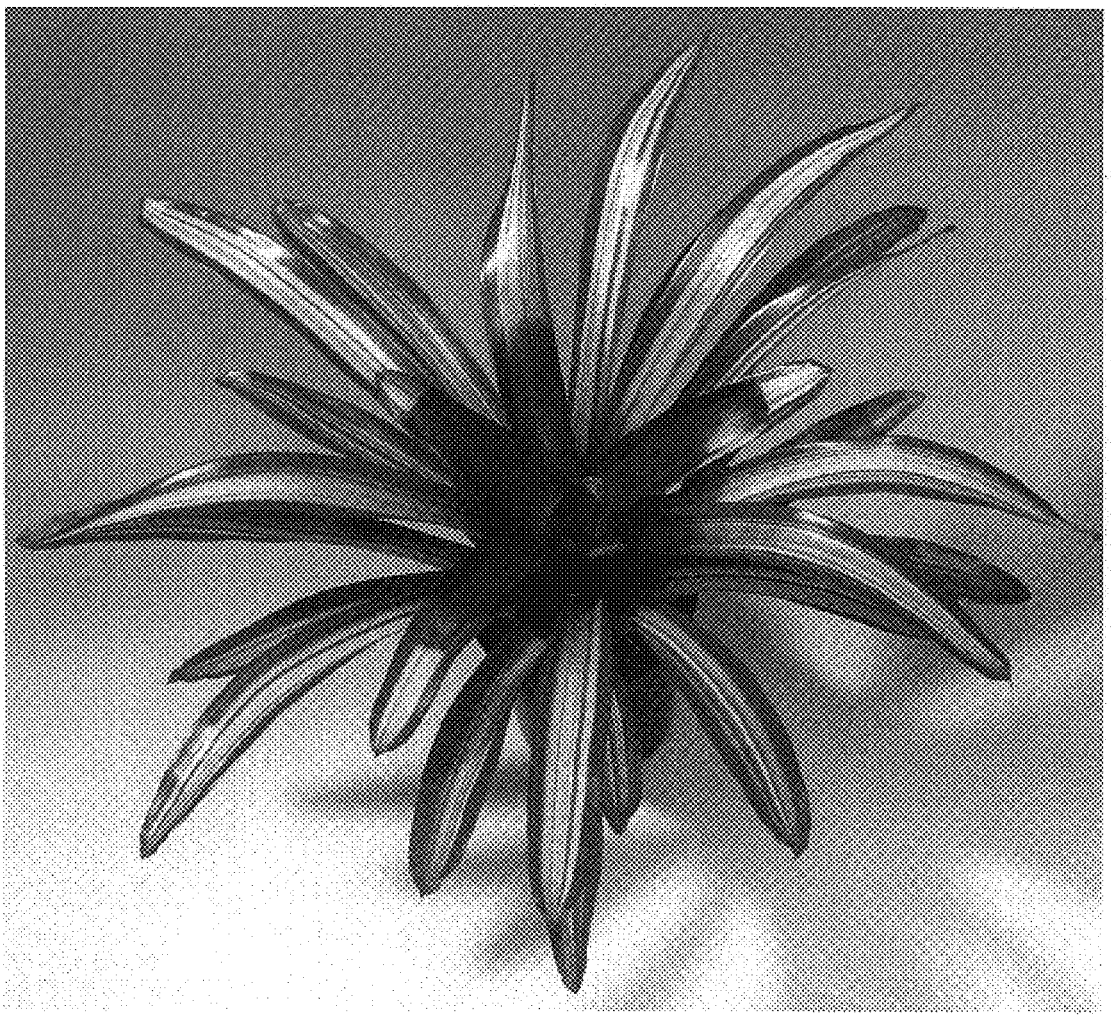

* * * * *